US011378634B2

(12) United States Patent
Scheffler et al.

(10) Patent No.: US 11,378,634 B2
(45) Date of Patent: Jul. 5, 2022

(54) MAGNETIC RESONANCE TOMOGRAPHY (MRT) IMAGING, EMPLOYING RF RECEIVE COILS WITH TEMPORAL SENSITIVITY PROFILE MODULATION

(71) Applicant: Max-Planck-Gesellschaft zur Foerderung der Wissenschaften e. V., Munich (DE)

(72) Inventors: Klaus Scheffler, Tuebingen (DE); Jonas Bause, Tuebingen (DE); Alexander Loktyushin, Tuebingen (DE); Kai Buckenmaier, Moessingen (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 73 days.

(21) Appl. No.: 16/984,853

(22) Filed: Aug. 4, 2020

(65) Prior Publication Data
US 2021/0048493 A1  Feb. 18, 2021

(30) Foreign Application Priority Data
Aug. 14, 2019  (EP) ..................................... 19191682

(51) Int. Cl.
*G01R 33/36* (2006.01)
*A61B 5/055* (2006.01)
(Continued)

(52) U.S. Cl.
CPC .......... *G01R 33/3671* (2013.01); *A61B 5/055* (2013.01); *G01R 33/5608* (2013.01); *A61B 5/0042* (2013.01)

(58) Field of Classification Search
CPC .. A61B 5/0042; A61B 5/055; G01R 33/3671; G01R 33/5608
See application file for complete search history.

(56) References Cited

U.S. PATENT DOCUMENTS 5,808,467 A   9/1998  Ochi et al.
7,423,430 B1  9/2008  Sharif et al.
(Continued)

FOREIGN PATENT DOCUMENTS

EP   2042881 B1    4/2011
WO   2004081518 A2 9/2004
WO   2012164595 A1 12/2012

OTHER PUBLICATIONS

Edelstein et al., "Spin warp NMR imaging and applications to human whole-body imaging", Physics in medicine & biology 25, No. 4, Letters to the Editor, pp. 751-756 (1980).
(Continued)

*Primary Examiner* — Gregory H Curran
(74) *Attorney, Agent, or Firm* — Caesar Rivise, PC (57) ABSTRACT

A method of magnetic resonance tomography includes arranging an object in a static magnetic field, subjecting it to radiofrequency (RF) pulses and magnetic field gradients for creating spatial encoding of magnetic resonance signals, acquiring the signals with at least two RF receive coils, each with a self-resonance frequency and a spatially restricted sensitivity profile, and reconstructing an object image. Spatial encoding of the signals by the gradients and the profiles is utilized, wherein the profile of at least one of the coils is subjected to a temporal sensitivity profile modulation while acquiring the signal. The self-resonance frequency of the at least one coil is set within a predetermined receive bandwidth of a constant resonance frequency value during the modulation. The reconstructing further utilizes the modulation for obtaining additional spatial information to the spatial encoding of the signals by the gradients. Furthermore, an MRI device is described.

19 Claims, 4 Drawing Sheets

(51) Int. Cl.
*G01R 33/56* (2006.01)
*A61B 5/00* (2006.01)

(56) References Cited

U.S. PATENT DOCUMENTS

| | | | |
|---|---|---|---|
| 8,581,588 B2 | 11/2013 | Driesel et al. | |
| 9,696,396 B2 | 7/2017 | Vitacolonna et al. | |
| 2007/0038068 A1 | 2/2007 | Leussler et al. | |
| 2010/0039111 A1* | 2/2010 | Luekeke | H01Q 21/065 324/318 |
| 2014/0210475 A1 | 7/2014 | Li et al. | |
| 2018/0286041 A1* | 10/2018 | Hu | G06T 7/0012 |

OTHER PUBLICATIONS

Griswold et al., "Generalized Autocalibrating Partially Parallel Acquisitions (GRAPPA)", Magnetic Resonance in Medicine, vol. 47, pp. 1202-1210 (2002).

Lauterbur, "Image Formation by Induced Local Interactions: Examples Employing Nuclear Magnetic Resonance", Nature, vol. 242, pp. 190-191 (1973).

Li et al., "Highly accelerated acquisition and homogeneous image reconstruction with rotating RF coil array at 7 T-A phantom based study", Journal of Magnetic Resonance, vol. 240, pp. 102-112 (2014).

Ljunggren, "A Simple Graphical Representation of Fourier-Based Imaging Methods", Journal of Magnetic Resonance, vol. 54, pp. 338-343 (1983).

Mansfield, "Multi-planar image formation using NMR spin echoes", J. Phys. C: Solid State Phys., vol. 10. pp. L55-L58 (1977).

Mansfield et al., "NMR 'diffraction' in solids?", J. Phys. C: Solid State Phys., vol. 6, pp. L422-L426 (1973).

Nemec et al., "Tunable terahertz metamaterials with negative permeability", Physical Review B, vol. 79, pp. 241108-1-241108-4 (2009).

Pruessmann et al., "SENSE: Sensitivity Encoding for Fast MRI", Magnetic Resonance in Medicine, vol. 42, pp. 952-962 (1999).

Shajan et al., "A 16-Channel Dual-Row Transmit Array in Combination with a 31-Element Receive Array for Human Brain Imaging at 9.4 T", Magnetic Resonance in Medicine, vol. 71, pp. 870-879 (2014).

Trakic et al. "A rapidly rotating RF coil for MRI." Concepts in Magnetic Resonance Part B: Magnetic Resonance Engineering: An Educational Journal 35, No. 2 (2009): 59-66.

Trakic et al., "Electromechanical Design and Construction of a Rotating Radio-Frequency Coil System for Applications in Magnetic Resonance", IEEE Transactions on Biomedical Engineering, vol. 59, No. 4, pp. 1068-1075 (2012).

Twieg, "The k-trajectory formulation of the NMR imaging process with applications in analysis and synthesis of imaging methods", Med Phys., vol. 10, No. 5, 610-21 (1983).

\* cited by examiner

MAGNETIC RESONANCE TOMOGRAPHY (MRT) IMAGING, EMPLOYING RF RECEIVE COILS WITH TEMPORAL SENSITIVITY PROFILE MODULATION

FIELD OF THE INVENTION

The invention relates to a method and to an apparatus for magnetic resonance tomography (MRT) imaging an object under investigation, e.g., a biological organism, like a patient or a test person, or a part thereof. Applications of the invention are available, e.g., in the fields of medical imaging or material investigations.

TECHNICAL BACKGROUND

In the present specification, reference is made to the following prior art illustrating technical background of the invention and related techniques:

[1] P. C. Lauterbur in "Nature" 242, 190-191 (1973);
[2] P. Mansfield et al. in "Journal of Physics C, Solid State Physics" 1973; 6, L422-L426;
[3] S. Ljunggren in "J. Magn. Reson." 1983; 54:338-343;
[4] D. B. Twieg in "Med. Phys." 1983; 10:610-621;
[5] W. A. Edelstein et al. in "Phys. Med. Biol." 25,751-756;
[6] K. P. Pruessmann et al. in "Magn. Reson. Med." 1999; 42:952-962;
[7] M. A. Griswold et al. in "Magn. Reson. Med." 2002; 47:1202-1210;
[8] G. Shajan et al. in "Magn. Reson. Med." 2014, 71(2):870-9;
[9] B. K. Trakic et al. in "Concepts Magn. Reson. Part B: Magn. Reson. Eng." 35B (2009) 59-66;
[10] M. Li et al. in "Journal of Magnetic Resonance" 240 (2014) 102-112; and
[11] H. Nemec et al. in "Phys. Rev. B" 79, 241108(R), 2009.

MRT imaging is a generally known imaging method for detecting spatially resolved MR signals from a spatially extended sample (object under investigation). If the sample is placed within a homogeneous field, a radiofrequency receive coil detects the sum of all signals originating from within the sample. No spatially resolved information is available. The principle of spatially resolved imaging is commonly based on the application of additional linear magnetic field gradients applied independently along the x, y and z axes ([1], [2]). With these gradients the local Larmor frequency of the magnetization becomes linearly dependent on its spatial position. Signals originating from different positions can be identified via their local frequency. Commonly a Fourier transformation is used to transform these frequencies into the spatial domain, i.e. an image in one, two or three dimensions is generated.

Using these linear gradients, the spatial composition of the object is acquired in frequency space, or k-space, which is the Fourier transformation of the object space ([3], [4]). Commonly the k-space is acquired in several consecutive steps. The most often used method is the spin warp technique in which k-space is scanned line-by-line using phase encoding gradients in one or two dimensions together with a readout gradient ([5]). However, this line-by-line scanning is a time-consuming process. Depending on the repetition time (TR) between consecutive line scans, which is in the order of 5 ms to 10 s, and the required resolution and further parameters, acquisition of a 2D or 3D image requires about 100 ms to several minutes.

Imaging speed in MRT imaging is of paramount importance, especially in clinical applications, for example to capture the beating heart or to measure blood flow dynamics. Therefore, several methods have been proposed to speed up the MR imaging process. The most successful and important method is parallel imaging that has revolutionized medical MR imaging and which is nowadays implemented in any commercial MR scanner. Parallel imaging is based on the concept of using instead of a single RF receive coil (that collects the sum of all magnetization within this coil) a set of several small RF receive coils. These small RF coils detect only a small portion of the object. Therefore, the local sensitivity profile of these small coils intrinsically provides spatial information of the origin of the magnetization. In parallel imaging, this local coil sensitivity information is used to speed up the imaging process by a factor 2 to 20, by combining the spatial information produced by linear gradients with the spatial information from local receive coils ([6], [7]).

It is generally known that RF receive coils used in MRT imaging, in particular in parallel imaging are tuned before the imaging process. Tuning comprises matching capacitances of the RF receive coils to the object to be imaged, e.g., a patient, and to the Larmor frequency of the MR scanner. During the imaging process, the tuning condition of the RF receive coils during receive intervals of coil operation is kept constant.

Dynamic RF sensing by mechanically moving the position of individual RF receive coils relative to the object has been suggested in [9] and [10] to increase imaging speed. Although dynamic RF sensing improves parallel imaging capabilities, it has several disadvantages. Mechanical movement of RF receive coils is technically very challenging to implement, and the speed of movement is very limited compared to the speed of an MR echo acquisition (milliseconds). Furthermore, the number of movable RF receive coils is limited, resulting in a restricted increase of the imaging speed. Due to these disadvantages, routine applications of conventional dynamic RF sensing have not yet been obtained.

OBJECTIVE OF THE INVENTION

It is an objective of the invention to provide an improved method of MRT imaging an object under investigation, being capable of avoiding limitations and disadvantages of conventional techniques. In particular, the method is to be capable of MRT imaging with further increased imaging speed, improved signal-to-noise-ratio and/or reduced mechanical complexity of employed devices. In particular, the MRT imaging method is to be suitable for routine applications in practice, e.g., in clinical applications. It is a further objective of the invention to provide an improved magnetic resonance imaging (MRI) device, being capable of avoiding limitations and disadvantages of conventional techniques. In particular, the MRI device is to be capable of accelerated MRT imaging, and/or it is to be provided with reduced complexity. Furthermore, the MRT imaging method and the MRI device are to be capable of creating the MR signals with an improved quality (e.g., increased signal to noise ratio, SNR) and/or with a reduced complexity of creating local gradient fields.

SUMMARY OF THE INVENTION

These objectives are solved by a method and/or a device comprising the features of the invention.

According to a first general aspect of the invention, the above objective is solved by a method of MRT imaging an object under investigation, comprising the steps of applying a static magnetic field to the object and subjecting the object to radiofrequency (RF) pulses and magnetic field gradients for creating spatial encoding of magnetic resonance signals. The RF pulses are created with at least one RF transmit coil. In response to the RF pulses, magnetic resonance signals are created in the object. Like in parallel imaging, the magnetic resonance signals are collected with at least two RF receive coils, each having a self-resonance frequency and a spatially restricted sensitivity profile (spatial sensitivity distribution). An object image (MR image) is reconstructed from the collected magnetic resonance signals. Due to the spatial encoding of the magnetic resonance signals by the magnetic field gradients and by the spatially restricted sensitivity profiles of the RF receive coils, a two- or three-dimensional MR image is obtained.

According to the invention, the sensitivity profile of at least one of the RF receive coils is subjected to a temporal sensitivity profile modulation. During the step of acquiring the magnetic resonance signals, the sensitivity profile of the at least one of the RF receive coils is temporally changed in a predetermined (controlled) manner, i. e. the shape, in particular the magnitude and/or phase, of the spatial sensitivity profile (spatial sensitivity distribution) relative to the RF receive coil is a function of time. Simultaneously, while modulating the sensitivity profile of the RF receive coil, the self-resonance frequency of the at least one modulated RF receive coil is set within a predetermined receive bandwidth of a constant resonance frequency value. Setting the self-resonance frequency of the at least one modulated RF receive coil within the predetermined receive bandwidth comprises keeping the self-resonance frequency constant or modulating it within the receive bandwidth. The receive bandwidth is equal or below +/−5% of the Larmor frequency is of the MR scanner. As an example, the self-resonance frequency of the at least one modulated RF receive coil can be varied by up to 1 to 5% around the Larmor frequency. In the following, if reference is made to a constant self-resonance frequency, it covers both cases of a frequency kept constant or modulated within the receive bandwidth. Preferably, each modulated RF receive coil has a fixed position relative to the object to be imaged, so that the sensitivity profile of the RF receive coil is temporally varied in a predetermined manner relative to the object. If the sensitivity profiles of two or more RF receive coils are modulated, each RF receive coil is modulated with a specific spatio-temporal modulation pattern. The modulation patterns of a plurality of modulated RF receive coils differ from each other. Furthermore, according to the invention, the step of reconstructing the object image further utilizes the temporal sensitivity profile modulation for obtaining additional spatial information further to the spatial encoding of the magnetic resonance signals by the magnetic field gradients. Advantageously, additional spatial information is obtained by each modulated RF receive coil, as the known sensitivity profile modulation specifically influences the collected magnetic resonance signals acquired with the modulated RF receive coil. Spatial information is impressed by the sensitivity profile modulation to the collected magnetic resonance signals, and this spatial information is used in the subsequent MR image reconstruction.

Preferably, reconstructing an object image m includes solving a linear equation system s=E m by a regularized optimization, wherein s includes the magnetic resonance signals and E is an encoding matrix being determined by the spatial encoding of the magnetic resonance signals and depending on time-varying modulation components.

According to a second general aspect of the invention, the above objective is solved by an MRI device, which includes a magnetic resonance scanner being configured for accommodating an object to be imaged, having a static magnetic field device for creating a static magnetic field, at least one RF transmit coil for creating at least one radiofrequency pulse, a gradient device being for creating magnetic field gradients, and at least two RF receive coils for collecting magnetic resonance signals. Each of the RF receive coils has a self-resonance frequency and a spatially restricted sensitivity profile. Furthermore, the MRI device includes a control device, implemented e.g., by a computer circuit, being configured for controlling the magnetic resonance scanner, and a reconstruction device, implemented e.g., by the same or a further computer circuit, being configured for reconstructing an object image based on the magnetic resonance signals.

According to the invention, the magnetic resonance scanner includes at least one modulation device, which is coupled with at least one of the RF receive coils. The modulation device is adapted for subjecting the sensitivity profile of the coupled RF receive coil to a temporal profile modulation during the step of acquiring the magnetic resonance signals, while keeping the self-resonance frequency constant (i. e. constant or varied by up to 1-5% around the Larmor frequency) during the temporal profile modulation. If multiple RF receive coils are modulated, multiple modulation devices are provided, each being assigned to one of the modulated RF receive coils. Each modulation device generally includes at least one component, which is electrically connected and/or electromagnetically coupled with the related RF receive coil and which is capable of changing the sensitivity profile of the RF receive coil. Furthermore, according to the invention, the reconstruction device is adapted for utilizing the temporal profile modulation of the at least one of the RF receive coils for obtaining spatial image information from the spatially encoded magnetic resonance signals, so that reconstructing the object image in particular includes utilizing the spatial image information from the sensitivity profile modulation. Preferably, the magnetic resonance scanner is configured for implementing the method of MRT imaging according to the first general aspect of the invention.

Advantageously, in contrast to conventional parallel imaging techniques, the invention uses dynamic instead of static RF sensitivity profiles. The parallel imaging technique using localized oscillating radio frequency fields is further improved by the local rapid variation of the sensitivity profile (magnitude and/or phase) of the RF receive coils while this RF receive coil acquires the magnetic resonance signal. The variation of the sensitivity profile is conducted in a time range equal to or below the duration of acquiring the magnetic resonance signals. A variation of the RF sensitivity profile(s) during the MR acquisition offers additional spatial information that is used for accelerated imaging (increased imaging speed), improving the signal-to-noise-ratio and/or for reducing the number of RF receive coils. Contrary to [9] and [10], the invention uses dynamically changing sensitivity profiles rather than rotating static sensitivity profiles. Advantageously, this allows to reduce the complexity of the RF receive coil arrangement. Furthermore, the restrictions of [9] and [10] are avoided with the invention as each single RF coil can be located at a fixed position relative to the object to be imaged. As an important result obtained by the inventors, the RF sensitivity profile can be modulated without changing (or with only minor changes of 1 to 5% around the Larmor frequency) the self-resonance frequency of the respective RF receive coil. Thus, the magnetic resonance signals are influenced by the spatial sensitivity modulation only, so that reconstructing the image is facilitated.

According to preferred embodiments of the invention, the RF sensitivity profile of the at least one of the RF receive coils is modified by electronically influencing the sensitivity profile. The temporal sensitivity profile modulation is created by at least one electronically driven modulation component coupled with the at least one modulated RF receive coil. Preferably, the sensitivity profile modulation is obtained by controlling drive voltages rather than control currents. Advantageously, there are several variants to achieve the electronically controlled RF sensitivity modulation, which can be provided alone or in combination as follows.

According to a first variant, the at least one modulation component comprises at least one tunable capacitor component of the at least one modulated RF receive coil. Generally, an RF receive coil comprises a curved or angular conductor loop that is made of conductor sections being separated by capacitors. The at least one tunable capacitor component is coupled with the conductor loop, in particular replacing one of the capacitors or being connected in parallel with at least one of the capacitors. The tunable capacitor component comprises e.g., a varactor diode or a digitally programmable capacitor. By controlling the tunable capacitor component with a driving modulation voltage, the sensitivity profile of the RF receive coil is tuned. One single tunable capacitor component can be provided at at least one of the RF receive coils, and/or multiple tunable capacitor components can be provided at at least one of the RF receive coils. The sensitivity profile modulation using the at least one tunable capacitor component has particular advantages in terms of a compact design of the RF receive coils and a facilitated control of the modulation thereof. Preferably, at least two tunable capacitor component are coupled with one conductor loop, so that keeping the self-resonance frequency of the RF receive coil is facilitated.

According to a second, alternative or additional variant, the at least one modulation component comprises at least one tunable metamaterial placed between the at least one modulated RF receive coil and the object to be imaged. The tunable metamaterial is a tunable grid arrangement made of tunable capacitors and inductances. Modulating the sensitive profile of at least one of the RF receive coils is obtained by modulating a spatial field transmission characteristic of the tunable metamaterial. Advantageously, the tunable metamaterial is capable of influencing the field distribution of the magnetic resonance signals collected with the RF receive coil in a spatially specific manner. Preferably, the tunable metamaterial being assigned to one of the RF receive coils is configured such that it does not influence the magnetic resonance signals collected with the other RF receive coil(s). Employing tunable metamaterial has the particular advantage of additional degrees of freedom in modulating the RF receive coil sensitivity profile(s).

According to a third, alternative or additional variant, the at least one modulation component comprises at least one auxiliary modulation coil, which is arranged adjacent to and electro-magnetically couples with at least one of the RF receive coils. The auxiliary modulation coil has a tunable sensitivity profile, which influences via the electro-magnetic coupling with the at least one of the RF receive coils the sensitive profile of at least one of the RF receive coils. Preferably, the at least one auxiliary modulation coil being assigned to one of the RF receive coils is configured such that it does not influence the magnetic resonance signals collected with the other RF receive coil(s). Employing at least one auxiliary modulation coil has the particular advantage of separating the control of a modulated coil from the magnetic resonance signal collection with the associated RF receive coil.

According to a further advantageous embodiment of the invention, the at least one electronically driven modulation component is controlled via wire connectors including blocking inductors or via opto-coupling. Advantageously, this reduces creation of field distortions within the magnetic resonance scanner and artefacts in MR imaging.

For the inventive increase of the imaging speed, providing one single modulated RF receive coil among the group of RF receive coils is sufficient. Preferably, the sensitivity profile of multiple RF receive coils is subjected to the temporal sensitivity profile modulation. In this case, the imaging speed can be further increased. All RF receive coils or some of the RF receive coils can be modulated. With preferred examples, the number of RF receive coils, to which the temporal sensitivity profile modulation is applied, is selected between 2 to 100, in particular 2 to 50. With practical applications, e.g., 4 to 8 RF receive coils can be provided. According to a particularly preferred embodiment, the temporal profile modulation of the sensitivity profiles of different RF receive coils have different spatiotemporal sensitivity patterns, like different magnitudes, frequencies, phases and/or modulation shapes. Advantageously, this allows introducing maximum additional spatial information into the image reconstruction.

If, according to a further variant of the invention, the temporal profile modulation has a periodic modulation shape, in particular a sine-shaped modulation, advantages for reconstruction the MR image can be obtained. Preferably, the temporal profile modulation has a modulation frequency in a range from 100 Hz to 1 MHz, e.g., in a range 10 kHz to 100 kHz. According to an alternative variant of the invention, the temporal profile modulation has a non-periodic modulation shape. Preferably, the sensitivity profile(s) is/are changed with a time scale equal to reciprocal values of the above modulation frequency. With non-periodic modulation, advantages are obtained in terms of reducing singularities of an inversion matrix used in reconstruction the MR image(s), resulting in less noise and artefacts in image reconstruction. In particular, the non-periodic temporal profile modulation may comprise a non-correlated noisy modulation and the elements of the inversion matrix may comprise random elements.

The inventive MRI device preferably includes local and static RF receive coils. With the RF receive coils being mechanically static coils, advantages for a compact scanner configuration are obtained. As a further advantage of the invention, at least one of the RF receive coils can be used as the at least one RF transmit coil.

BRIEF DESCRIPTION OF THE DRAWINGS

Further advantages and details of the invention are described in the following with reference to the attached drawings, which schematically show in.

DETAILED DESCRIPTION OF PREFERRED EMBODIMENTS OF THE INVENTION

Embodiments of the invention are described in the following with particular reference to the inventive locally specific sensitivity profile modulation of at least one MR receive coil. The invention preferably is implemented with an MR scanner as it is known per se.

Accordingly, details of the MR scanner, the available control schemes thereof and available schemes of MR signal acquisition are not described as they are known from prior art. Detailed exemplary reference is made to applications of the invention, wherein sensitivity profile modulation is implemented by connecting controllable varactor diodes in parallel to capacitances of an RF receive coil loop. The invention is not restricted to this embodiment, but correspondingly can be implemented with other types of electronically driven modulation components, like tunable metamaterials. Furthermore, the invention is not restricted to the described examples of 2 or 16 channel RF receive coils, but can be implemented with other numbers of RF receive coils, like 32 RF receive coils, e.g., on a helmet shaped carrier for imaging a patient's head. The RF receive coils can be provided with individual local sensitivity profiles as a group of separate coils or as a fixed array of loops.

Embodiments of the MRI Device and Method

Figure 1:
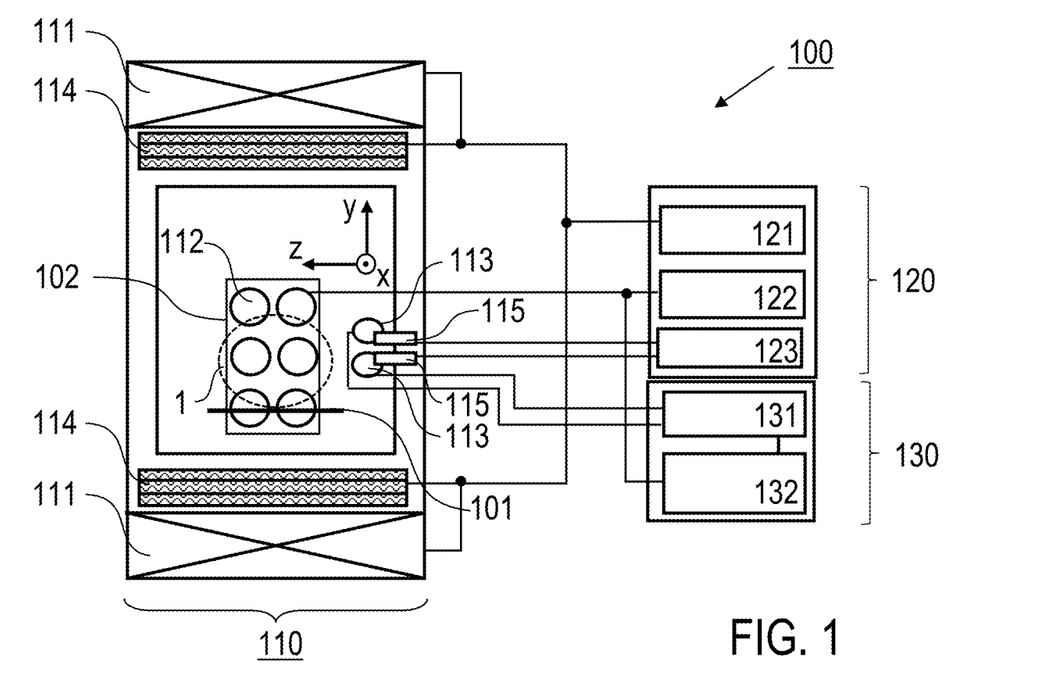
FIG. 1: an MRI device according to an embodiment of the invention.

FIG. 1 schematically illustrates an embodiment of an MRI device 100 including an MR scanner 110, a control device 120 and a reconstruction device 130, which are configured for implementing the invention. The MR scanner 110 includes a main magnetic field device 111 for creating a homogeneous static magnetic field, e.g., 9.4 T or 4 T, a magnetic gradient device 114 for creating spatially encoding magnetic field gradients, an array 102 of RF transmit coils 112 (or alternatively a single RF transmit coil) and at least two RF receive coils 113. The RF receive coils 113 are shown with a distance from the RF transmit coils 112 for illustration purposes only. In practice, RF receive coils 113 are arranged directly adjacent to, in particular below, the RF transmit coils 112. Preferably, the RF transmit coils have non-overlapping sensitivity profiles and the RF receive coils have non-overlapping sensitivity profiles. Furthermore, a holding device 101, like a supporting table, can be provided for supporting an object 1 to be investigated. The components 111, 112, 114 and 101 can be configured as it is known from conventional MR scanners. All RF transmit and receive coils can be arranged on a common carrier, like the carrier 101. The RF receive coils 113 are described with further details below with reference to FIGS. 3 and 6.

Figure 3:
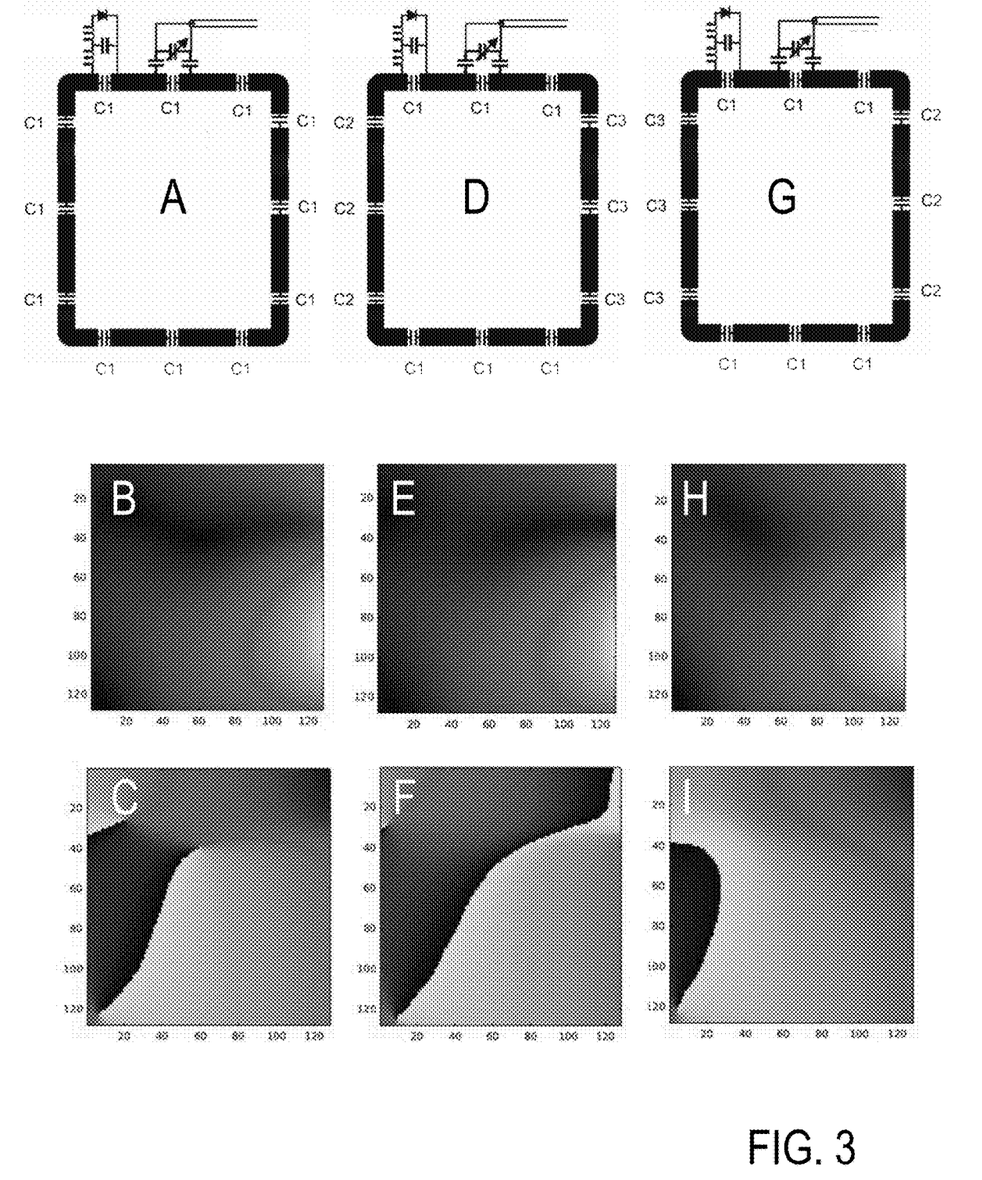
FIG. 3: an illustration of influencing sensitivity profiles by changing coupling capacitors within RF receive coils.
Figure 4:
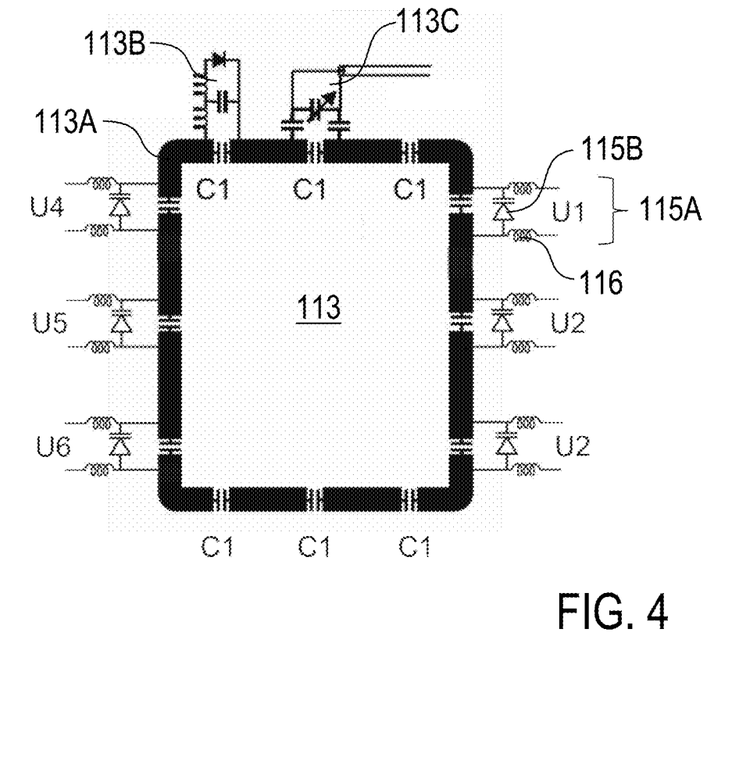
FIG. 4: an example of an RF receive coil with electronically driven modulation components being adapted for a sensitivity profile modulation.
Figure 5:
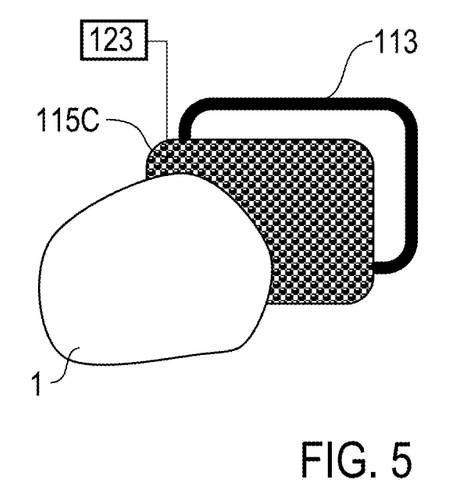
FIGS. 5 and 6: further examples of electronically driven modulation components.

The magnetic resonance scanner 110 includes schematically shown modulation devices 115, each of which being coupled with one of the RF receive coils 113. The modulation devices 115 are adapted for temporally changing the sensitivity profile of the RF receive coils 113 with different modulation patterns, while collecting magnetic resonance signals. Examples of the modulation devices 115 are shown in FIGS. 3 to 5.

The control device 120 includes a main field and gradient control unit 121, an RF pulse control unit 122 and a profile modulation control unit 123, each including driving circuits, like excitation and modulation voltage or current sources, amplifiers and/or pulse modulators, and at least one computer unit. The profile modulation control unit 123 is connected with the modulation devices 115 for creating the inventive sensitivity profile modulation. The components 121 to 123 can be provided with a common computer unit or with separate computer units, coupled with the driving circuits for driving the components 111, 112, 114 and 115. The profile modulation control unit 123 comprises e.g., a tunable voltage source with a number of output channels each being connected with one of the modulation devices 115.

The reconstruction device 130 includes a signal acquisition device 131 coupled with the RF receive coils 113 and a calculation device 132. Optionally, the calculation device 132 can be coupled, e.g., via direct connection or any other type of data transmission, with the profile modulation control unit 123, so that information on the modulation pattern applied to the modulation devices 115 can be introduced in the MR image reconstruction. The components 131 and 132 can be provided with a common computer unit or with separate computer units. The computer units of the control device 120 and the reconstruction device 130 are adapted for running software controlling the setting of the components 111 to 115, for collecting and processing MR signals and for MR image reconstruction, resp.

Figure 2:
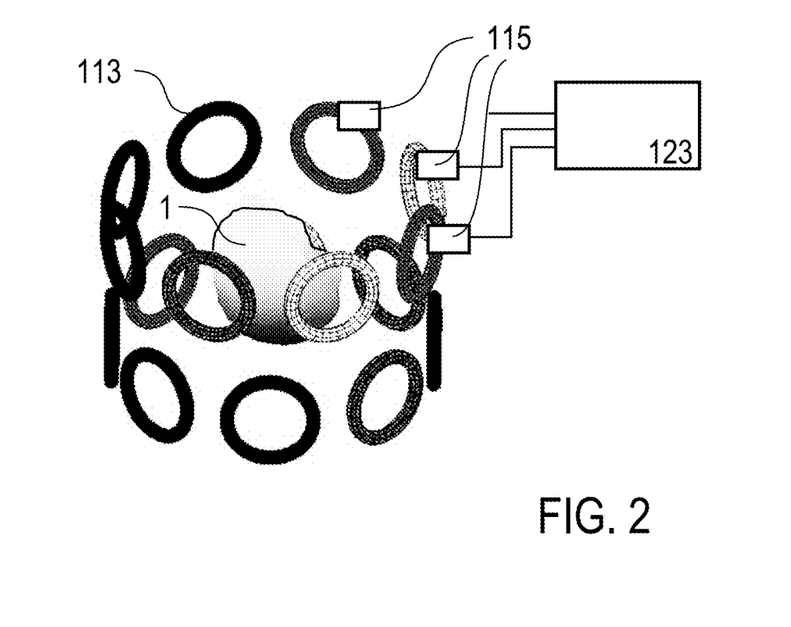
FIG. 2: an illustration of the provision of multiple RF receive coils.

FIG. 2 schematically shows an example of a 16 channel receive array including 16 RF receive coils 113, which are arranged in two circular rows around the object 1 to be imaged. The RF receive coils 113 are fixed on a common carrier (not shown). Each of the RF receive coils 113 has a modulation device 115 being connected with the profile modulation control unit 123 (shown with 3 examples only).

Generally, the RF receive coils 113, e.g., according to the example of FIG. 2, additionally can be used as RF transmit coils 112. With this embodiment of the invention, RF coils operable as RF transmit and receive coils are connected with both of the RF pulse control unit 122 and the profile modulation control unit 123. As the acquisition of magnetic resonance signals with the inventive sensitivity profile modulation occurs with a delay (e.g., 1 to 5 ms) after the excitation of the object by transmitting RF pulses (duration about 1 to 5 ms), switching between the transmit and receive functions can be provided. During the excitation of the object, the sensitivity profile modulation is switched of.

A first embodiment of implementing the sensitivity profile modulation is described with reference to FIGS. 3 and 4. FIG. 3A shows an example of a conventional configuration of an RF receive coil having a conductor loop of loop sections separated by capacitors C1.

Capacitors C1 are identical and distributed along the coil. Below the coil of FIG. 3A are the resulting simulated and measured coil sensitivity maps shown as B1 magnitude (FIG. 3B) and phase (FIG. 3C). Accordingly, this conventional coil produces a static, but distinct spatial sensitivity pattern. FIGS. 3D and 3G show asymmetric coils where different capacitors C2 and C3 are used. Capacitors C2 and C3 are adjusted such that the entire coil has the same resonance frequency (or about the same 1 to 5%) as in FIG. 3A. For example, all three coils of FIG. 3A, 3D and 3G are tuned to 400 MHz, C1 is 4.7 pF, C2 is 1.8 pF and C3 is 62 pF. The corresponding sensitivity profiles are shown in FIGS. 3E (amplitude) and 3F (phase) for the asymmetric configuration of FIG. 3D and in FIGS. 3H (amplitude) and 3I (phase) for the asymmetric configuration of FIG. 3G. This demonstrates that changing certain capacitors while keeping the self-resonance frequency constant will alter the resulting sensitivity map of the coil. The static examples of FIG. 3 are shown for illustration purposes only. A fast and dynamic modification of the sensitivity profile can be achieved with adjustable capacitors, for example, with varactor diodes, as shown in FIG. 4.

FIG. 4 illustrates an RF receive coil 113, comprising a loop with loop sections 113A being separated by static capacitors C1 or tunable capacitor components 115A. Two of the static capacitors C1 are connected in parallel with an active detuning circuit 113B for matching the RF receive coil 113 to the object to be imaged and an RF in/out-coupling circuit 113C connected with the signal acquisition device 131 (and, if the RF receive coil is also used as transmit coil, with the RF pulse control unit 122), see FIG. 1. While FIG. 4 shows an example with six tunable capacitor components 115A, less (at least one, preferably at least two) or more capacitor components can be provided with other applications.

The tunable capacitor components 115A each include a capacitor with a parallel connected varactor diode 115B having a voltage-dependent capacity. Preferably, the varactor diodes 115B are connected via blocking inductors 116 with the profile modulation control unit 123 (see FIG. 1). Alternatively, opto-couplers can provided instead of the blocking inductors 116. The tunable capacitor components 115A including the varactor diodes 115B provide the modulation device 115 used for modulating the sensitivity profile of the RF receive coil 113. The capacity of the varactor diodes 115B is adjusted by application of different driving voltages U1 to U6 (or more) to the varactor diodes 115B. With the adjustment of the varactor diodes 115B, the capacitance of the capacitor components 115A can be changed. Accordingly, the resulting sensitivity profiles of the RF receive coil 113 can be modified dynamically.

The capacitance values of the capacitor components 115A are tuned such that the self-resonance frequency of the RF receive coil 113 is kept constant (or 1 to 5%) during modulation. Accordingly, the capacitor components 115A are not modulated independently from each other. The capacitor components 115A preferably are modulated with a pairwise mutual relationship such that the self-resonance frequency of the RF receive coil 113 is kept constant. Thus, preferably an even number of capacitor components 115A is provided. The appropriate temporal modulation pattern, in particular temporal function of driving voltages and mutual phases thereof, is found in practical applications of the invention on the basis of prior numerical simulations, reference values from prestored tables and/or prior calibrations measurements.

With a preferred example, the sensitivity profiles are modulated during signal acquisition, i. e. during sampling the k space, with a temporal modulation pattern having periodic changes of the driving voltages of the capacitor components 115A with equal or different modulation frequencies, e.g., of 40 kHz.

Figure 6:
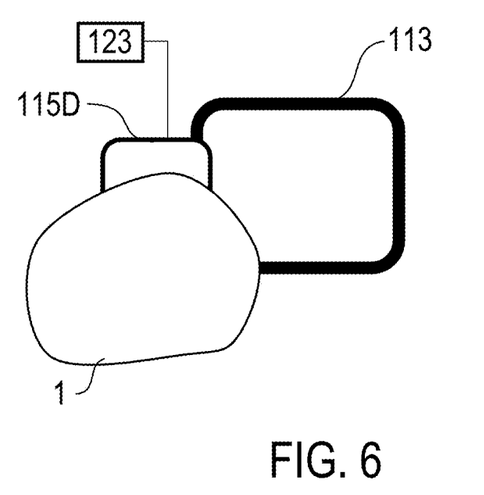

FIGS. 5 and 6 show further embodiments of implementing the sensitivity profile modulation with electronically driven modulation components. According to FIG. 5, at least one tunable metamaterial 115C is arranged as a field shaping shield between at least one of the RF receive coils 113, e.g., according to FIG. 2A or FIG. 4A, and the object 1.

Examples of tunable metamaterials are described e.g., in [11]. With a grid arrangement made of tunable capacitors and inductances, the dielectric permittivity and magnetic permeability can be adjusted by application of electric fields or optical switching. To this end, the tunable metamaterial is connected with the profile modulation control unit 123 creating driving voltages for tuning the metamaterial. With the tunable metamaterial being placed between the RF receive coil 113 and the object 1, the resulting sensitivity profile within the object can be dynamically modified. A suitable configuration of the metamaterial is selected in dependency on the particular application conditions, e.g., based on numerical simulations. Instead of one metamaterial per RF receive coil, more than one metamaterial can be provided for modulating the sensitivity profile of the RF receive coil.

According to FIG. 6, at least one auxiliary modulation coil 115D is arranged as a field shaping component with electro-magnetic coupling with one of the RF receive coils 113, e.g., according to FIG. 2A or FIG. 4A, and the object 1. The auxiliary modulation coil 115D comprises e.g., an RF coil like the RF receive coil 113, and it is connected with the profile modulation control unit 123. By modulating the sensitivity profile of the auxiliary modulation coil 115D, the effective sensitivity profile of the signal collecting RF receive coil 113 is modulated.

Image Reconstruction

The inventive spatial encoding relies on dynamically modifying the RF sensitivity profile of at least one of the RF receive coils. The technique allows using characteristic spatiotemporal patterns of sensitivity profile variations during image acquisition in order to improve SNR or accelerate the acquisition. In the following the model of the image acquisition is specified (notations adapted from [6]).

Consider an imaging process using an array of $N_c$ RF receive coils 113 with independently tunable complex and spatially varying sensitivity profiles $s_{i,j}(r)$ ($i=1 \ldots N_c$). Fourier encoding is described by a set of $N_k$ sampling positions in k-space that are sampled at time point $t_j$ ($j=1 \ldots N_k$). Let the whole object 1 be within the volume of interest (VOI). Then a sample value $S_{i,j}$ obtained from the i-th coil at the j-th position in k-space is given by $$S_{i,j} = \int_{r \in VOI} m(r)\exp(-ik_j r)s_{i,j}(r)dr$$

r is the spatial 3D position within VOI, and m(r) is the complex valued image in spatial domain that needs to be reconstructed.

The sensitivity profiles $s_{i,j}(r)$ vary in time (denoted by the index j that corresponds to a certain time point $t_j$ which is also related to the measured k-space position $k_j$) and space (through r). A signal $S_{i,j}$ acquired at time $t_j$ for coil i can be obtained via the integration over the excited volume of interest, VOI.

In order to reconstruct the image m(r) the following linear system has to be solved: S=Em. Here, E is the linear operator that aggregates the exponential encoding terms and performs the summation (integration) over the spatial domain. m is the complex valued image m(r) evaluated on discrete grid positions within the VOI. Since the encoding matrix E is prohibitively large for inversion and to improve stability of reconstruction, the following regularized optimization problem is solved:

$$\hat{m} = \mathrm{argmin}_m (\|Em-S\|_2^2 + \lambda \|Dm\|_1)$$

The regularization coefficient λ sets the weight of the total variation term that penalizes high-frequency artifacts in the reconstruction. A computationally intensive part in the optimization loop is the repetitive multiplications with an encoding matrix E, which can either be pre-computed and stored in memory, or generated online. In the latter case, the operation can be efficiently performed on GPUs, since it relies on computing a massive number of independent complex-valued weighting coefficients subject to spatial location.

Simulation and Test Results

Figure 7:
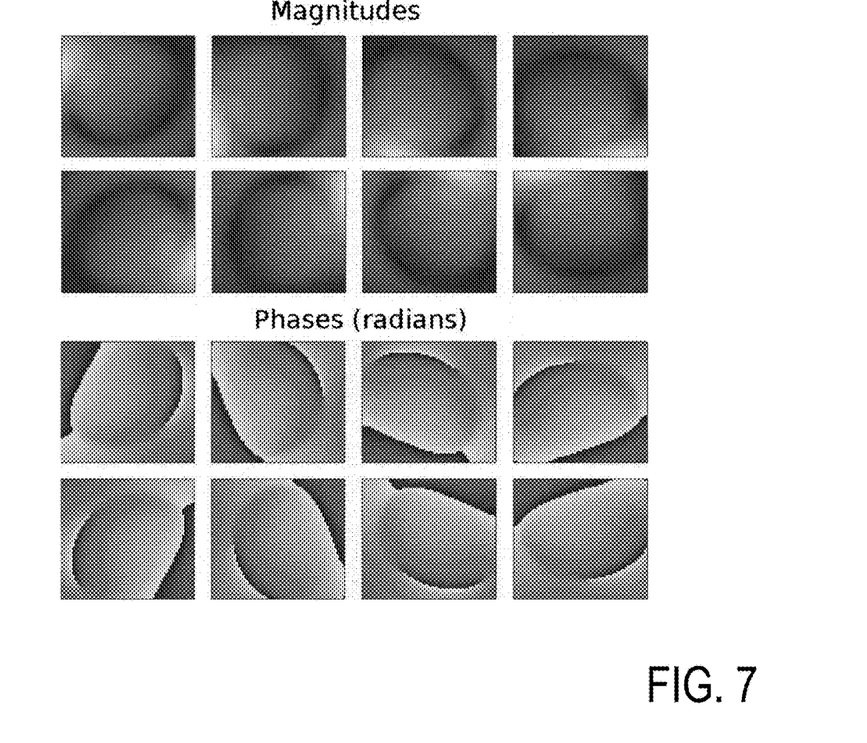
FIG. 7: synthesized 8 coil magnitude (top) and phase (bottom) sensitivity profiles based on experimental measurements of coils E and F from FIG. 5.
Figure 8:
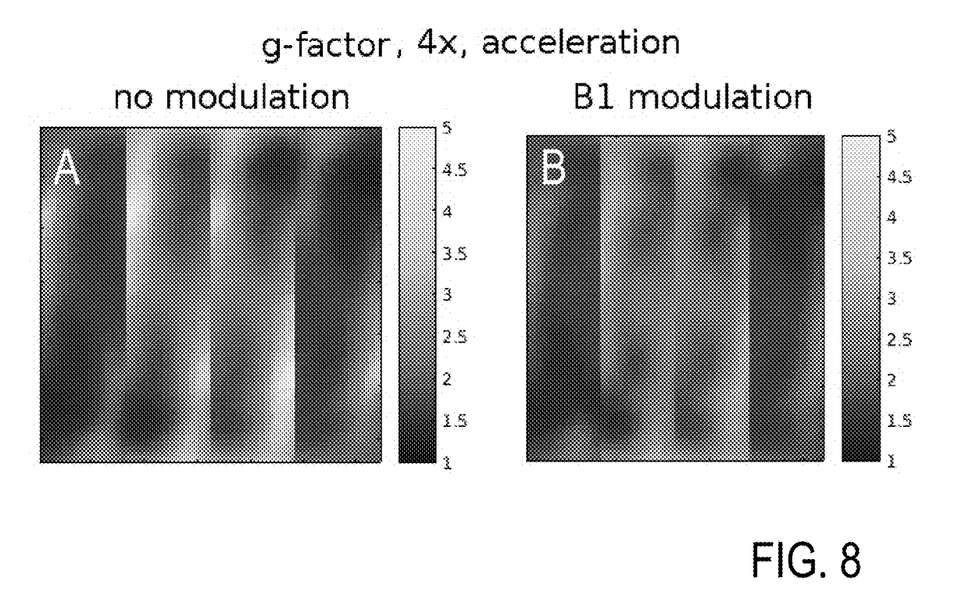
FIG. 8: g-factor maps for static and dynamic image reconstruction.

Experimental coil sensitivity maps were acquired with the two asymmetric coils shown in FIGS. 3D and 3G. This single-coil sensitivity map was then numerically repeated for 8 different positions around a cylindrical phantom, as shown in FIG. 7, which shows synthesized 8 coil magnitude (top) and phase (bottom) sensitivity profiles. Using these 8 coil sensitivity maps a g-factor map (that describes the quality of acceleration) was calculated based on static coil sensitivities and dynamically alternated coil sensitivity profiles. For dynamically modulated coil sensitivities, each coil sensitivity profile was alternated between sensitivity of FIG. 3E to FIG. 3H and between sensitivity of FIG. 3F to FIG. 3I for each consecutive acquisition step along each k-space scan line. In FIG. 8, the resulting static (FIG. 8A) and dynamic (FIG. 8B) g-factor maps are shown. The lower g-factor maps represent higher reconstruction quality, which is the case for the inventive using of RF receive coil modulation.

The features of the invention disclosed in the above description, the drawings and the claims can be of significance both individually as well as in combination or sub-combination for the realization of the invention in its various embodiments.

What is claimed is:

1. A method of magnetic resonance tomography (MRT) imaging an object, comprising the steps of:
    arranging the object in a static magnetic field;
    subjecting the object to radiofrequency (RF) pulses and magnetic field gradients for creating spatial encoding of magnetic resonance signals;
    acquiring the magnetic resonance signals with at least two RF receive coils, each with a self-resonance frequency and a spatially restricted sensitivity profile; and
    reconstructing an object image, wherein the spatial encoding of the magnetic resonance signals by the magnetic field gradients and by spatially restricted sensitivity profiles of the RF receive coils is utilized, wherein:
    the spatially restricted sensitivity profile of at least one of the RF receive coils is subjected to a temporal sensitivity profile modulation during the step of acquiring the magnetic resonance signals, wherein the spatially restricted sensitivity profile of the at least one of the RF receive coils is temporally changed relative to the at least one of the RF receive coils as a function of time and the self-resonance frequency of the at least one modulated RF receive coil is set within a predetermined receive bandwidth of a constant resonance frequency value during the temporal sensitivity profile modulation, and
    the step of reconstructing the object image further utilizes the temporal sensitivity profile modulation for obtaining additional spatial information to the spatial encoding of the magnetic resonance signals by the magnetic field gradients.

2. The MRT imaging method according to claim 1, wherein the temporal sensitivity profile modulation is created by at least one electronically driven modulation component coupled with the at least one modulated RF receive coil.

3. The MRT imaging method according to claim 2, wherein the at least one modulation component comprises at least one tunable capacitor component of the at least one modulated RF receive coil.

4. The MRT imaging method according to claim 3, wherein the at least one modulation component comprises at least one tunable capacitor component of the at least one modulated RF receive coil with at least one of at least one varactor diode and at least one digitally programmable capacitor.

5. The MRT imaging method according to claim 3, wherein the at least one modulation component is controlled via wire connectors including blocking inductors or via opto-coupling.

6. The MRT imaging method according to claim 2, wherein the at least one modulation component comprises at least one tunable metamaterial placed between the at least one modulated RF receive coil and at least one of the object and at least one auxiliary modulation coil.

7. The MRT imaging method according to claim 6, wherein the at least one modulation component is controlled via wire connectors including blocking inductors or via opto-coupling.

8. The MRT imaging method according to claim 1, wherein:
    the sensitivity profile of multiple RF receive coils is subjected to the temporal sensitivity profile modulation, and
    the temporal profile modulation of the sensitivity profiles of different RF receive coils have different spatiotemporal sensitivity patterns.

9. The MRT imaging method according to claim 8, wherein the temporal profile modulation of the sensitivity profiles of different RF receive coils have at least one of different magnitudes, frequencies, phases and modulation shapes.

10. The MRT imaging method according to claim 1, wherein the temporal profile modulation has a periodic modulation shape.

11. The MRT imaging method according to claim 1, wherein the temporal profile modulation has a non-periodic modulation shape.

12. The MRT imaging method according to claim 1, wherein the RF receive coils have at least one of the features:
    the RF receive coils are mechanically static coils;
    the RF receive coils, to which the temporal sensitivity profile modulation is applied, are provided in a quantity from 2 to 100; and
    the temporal profile modulation has a modulation frequency in a range from 100 Hz to 1 MHz.

13. The MRT imaging method according to claim 1, wherein at least one of the RF receive coils is used as the at least one RF transmit coil.

14. The MRT imaging method according to claim 1, wherein the step of reconstructing the object image m includes solving a linear equation system s=E m by a regularized optimization, wherein s includes the magnetic resonance signals and E is an encoding matrix being determined by the spatial encoding of the magnetic resonance signals and depending on time-varying modulation components.

15. A magnetic resonance imaging (MRI) device, comprising:
- a magnetic resonance scanner being configured for accommodating an object to be imaged, including a static magnetic field device being configured for creating a static magnetic field, at least one RF transmit coil being configured for creating RF pulses, at least two RF receive coils, each having a self-resonance frequency and a spatially restricted sensitivity profile and being configured for acquiring magnetic resonance signals, and a gradient device being configured for creating magnetic field gradients;
- a control device being configured for controlling the magnetic resonance scanner; and
- a reconstruction device being configured for reconstructing an object image based on the acquired magnetic resonance signals, wherein:
- the magnetic resonance scanner includes at least one modulation device, which is further adapted for subjecting the sensitivity profile of at least one of the RF receive coils to a temporal profile modulation during the step of acquiring the magnetic resonance signals, wherein the sensitivity profile of the at least one of the RF receive coils is temporally changed relative to the at least one of the RF receive coils as a function of time and the self-resonance frequency is set within a predetermined receive bandwidth of a constant resonance frequency value; and
- the reconstruction device is configured for reconstructing the object image by utilizing the temporal profile modulation for obtaining spatial image information from the spatially encoded magnetic resonance signals.

16. The MRI device according to claim 15, wherein the at least one modulation device comprises an electronically driven modulation component coupled with the at least one modulated RF receive coil.

17. The MRI device according to claim 16, wherein the modulation component includes at least one of:
- at least one tunable capacitor component of the at least one modulated RF receive coil;
- at least one tunable metamaterial being placed between the at least one modulated RF receive coil and the object; and
- at least one auxiliary modulation coil.

18. The MRI device according to claim 16, further comprising wire connectors including blocking inductors or opto-couplers being arranged for controlling the at least one modulation device.

19. A magnetic resonance imaging (MRI) device, comprising:
- a magnetic resonance scanner being configured for accommodating an object to be imaged, including a static magnetic field device being configured for creating a static magnetic field, at least one RF transmit coil being configured for creating RF pulses, at least two RF receive coils, each having a self-resonance frequency and a spatially restricted sensitivity profile and being configured for acquiring magnetic resonance signals, and a gradient device being configured for creating magnetic field gradients;
- a control device being configured for controlling the magnetic resonance scanner; and
- a reconstruction device being configured for reconstructing an object image based on the acquired magnetic resonance signals, wherein:
- the magnetic resonance scanner includes at least one modulation device, which is further adapted for subjecting the sensitivity profile of at least one of the RF receive coils to a temporal profile modulation during the step of acquiring the magnetic resonance signals, wherein the spatially restricted sensitivity profile of the at least one of the RF receive coils is temporally changed relative to the at least one of the RF receive coils as function of time and the self-resonance frequency is set within a predetermined receive bandwidth of a constant resonance frequency value;
- the reconstruction device is configured for reconstructing the object image by utilizing the temporal profile modulation for obtaining spatial image information from the spatially encoded magnetic resonance signals; and
- the MRI device is configured to conduct the MRT imaging method according to claim 1.

* * * * *